(12) United States Patent
Jung et al.

(10) Patent No.: US 11,331,091 B2
(45) Date of Patent: May 17, 2022

(54) SURGICAL INSTRUMENT SET FOR USE DURING UNILATERAL BIPORTAL ENDOSCOPY

(71) Applicants: ENDOVISION CO., LTD., Daegu (KR); Min Ho Jung, Daegu (KR); Sang-Kyu Son, Busan (KR)

(72) Inventors: Min Ho Jung, Daegu (KR); Sang-Kyu Son, Busan (KR)

(73) Assignees: Endovision Co., Ltd.; Min Ho Jung; Sang-Kyu Son

( * ) Notice: Subject to any disclaimer, the term of this patent is extended or adjusted under 35 U.S.C. 154(b) by 593 days.

(21) Appl. No.: 15/879,825

(22) Filed: Jan. 25, 2018

(65) Prior Publication Data

US 2019/0142408 A1 May 16, 2019

(30) Foreign Application Priority Data

Nov. 14, 2017 (KR) .................. 10-2017-0151636
Jan. 23, 2018 (KR) .................. 10-2018-0008451

(51) Int. Cl.
*A61B 17/02* (2006.01)
*A61B 17/16* (2006.01)
(Continued)

(52) U.S. Cl.
CPC ........ *A61B 17/025* (2013.01); *A61B 1/00091* (2013.01); *A61B 1/00135* (2013.01); *A61B 1/00195* (2013.01); *A61B 1/015* (2013.01); *A61B 1/045* (2013.01); *A61B 17/02* (2013.01); *A61B 17/1615* (2013.01); *A61B 17/8861* (2013.01); *A61B 18/14* (2013.01); *A61B 90/02* (2016.02); *A61F 2/4611* (2013.01); *A61F 2/4644* (2013.01); *A61B 17/1671* (2013.01);
(Continued)

(58) Field of Classification Search
CPC ... A61B 17/025; A61B 90/02; A61B 1/00091; A61B 1/00135; A61B 17/02; A61B 17/8861; A61B 18/14; A61B 50/36; A61B 17/16; A61B 17/3211; A61F 2/4611; A61F 2/4644
See application file for complete search history.

(56) References Cited

U.S. PATENT DOCUMENTS 4,934,352 A * 6/1990 Sullivan, Jr. ........... A61B 17/02
600/213
5,144,942 A * 9/1992 Decarie .............. A61B 1/00144
206/363

(Continued)

FOREIGN PATENT DOCUMENTS

KR        101441320 B1 * 9/2014 ............. A61B 17/70
WO   WO-2004032783 A1 * 4/2004 ............. A61B 50/31
WO   WO-2006059189 A1 * 6/2006 .......... A61M 3/0258

*Primary Examiner* — Aaron B Fairchild
*Assistant Examiner* — Shankar Raj Ghimire
(74) *Attorney, Agent, or Firm* — Mendelsohn Dunleavy, P.C.

(57) ABSTRACT

Disclosed is a method of unilateral biportal endoscopy and a surgical instrument set used in the same. More particularly, the present invention relates to a method of unilateral biportal endoscopy which separately secures a working portal for surgical instruments and an endoscopic portal for an endoscope, thereby providing a more accurate spinal surgery, and to a surgical instrument set which can be effectively applied to the method.

4 Claims, 11 Drawing Sheets

(51) Int. Cl.
*A61F 2/46* (2006.01)
*A61B 18/14* (2006.01)
*A61B 17/88* (2006.01)
*A61B 1/00* (2006.01)
*A61B 1/045* (2006.01)
*A61B 1/015* (2006.01)
*A61B 90/00* (2016.01)
*A61B 17/00* (2006.01)
*A61B 17/32* (2006.01)
*A61B 17/17* (2006.01)
*A61M 29/00* (2006.01)
*A61B 50/33* (2016.01)
*A61B 18/00* (2006.01)
*A61B 50/20* (2016.01)
*A61B 17/3211* (2006.01)

(52) U.S. Cl.
CPC ....... *A61B 17/1757* (2013.01); *A61B 17/3211* (2013.01); *A61B 50/20* (2016.02); *A61B 50/33* (2016.02); *A61B 2017/00429* (2013.01); *A61B 2017/00477* (2013.01); *A61B 2017/0256* (2013.01); *A61B 2017/1602* (2013.01); *A61B 2017/320008* (2013.01); *A61B 2018/00601* (2013.01); *A61B 2018/1495* (2013.01); *A61B 2217/005* (2013.01); *A61B 2217/007* (2013.01); *A61F 2002/4681* (2013.01); *A61M 29/00* (2013.01)

(56) References Cited

U.S. PATENT DOCUMENTS

| | | | | |
|---|---|---|---|---|
| 5,158,543 A * | 10/1992 | Lazarus | A61B 17/3417 | 604/164.1 |
| 5,315,985 A * | 5/1994 | Decarie | A61B 1/00144 | 600/101 |
| 5,453,094 A * | 9/1995 | Metcalf | A61B 17/3417 | 206/366 |
| 5,472,426 A * | 12/1995 | Bonati | A61B 17/1604 | 600/564 |
| 5,741,261 A * | 4/1998 | Moskovitz | A61B 17/1606 | 606/79 |
| 5,743,853 A * | 4/1998 | Lauderdale | A61B 17/02 | 600/210 |
| 6,096,026 A * | 8/2000 | Schultz | A61B 17/00234 | 600/240 |
| 6,241,734 B1 * | 6/2001 | Scribner | A61B 17/8855 | 606/93 |
| 6,371,968 B1 * | 4/2002 | Kogasaka | A61B 17/00234 | 600/201 |
| 6,405,863 B1 * | 6/2002 | Dhindsa | B65D 1/36 | 206/370 |
| 6,412,639 B1 * | 7/2002 | Hickey | A61B 50/30 | 206/438 |
| 6,443,990 B1 * | 9/2002 | Aebi | A61F 2/4601 | 623/17.16 |
| 6,564,078 B1 * | 5/2003 | Marino | A61B 5/04012 | 600/373 |
| 6,582,441 B1 * | 6/2003 | He | A61N 1/05 | 604/164.01 |
| 6,613,054 B2 * | 9/2003 | Scribner | A61B 17/8855 | 606/93 |
| 6,755,815 B2 * | 6/2004 | Schultz | A61B 17/00234 | 606/1 |
| 7,226,451 B2 * | 6/2007 | Shluzas | A61B 1/00149 | 600/219 |
| 7,632,284 B2 * | 12/2009 | Martinek | A61B 17/0682 | 606/142 |
| 7,657,308 B2 * | 2/2010 | Miles | A61B 5/4041 | 600/546 |
| 8,000,782 B2 * | 8/2011 | Gharib | A61B 1/32 | 600/546 |
| 8,361,078 B2 * | 1/2013 | Beyar | A61B 17/7095 | 606/94 |
| 8,454,644 B2 * | 6/2013 | McDonnell | A61M 29/00 | 606/190 |
| 8,568,317 B1 * | 10/2013 | Gharib | A61B 8/4483 | 600/437 |
| 8,597,360 B2 * | 12/2013 | McLuen | A61F 2/44 | 623/17.16 |
| 8,690,761 B2 * | 4/2014 | Begemann | A61M 3/0283 | 600/114 |
| 8,894,658 B2 * | 11/2014 | Linderman | A61B 17/8819 | 606/86 R |
| 8,951,261 B2 * | 2/2015 | Sharkey | A61B 17/1637 | 606/92 |
| 9,119,646 B2 * | 9/2015 | Sharkey | A61B 6/505 | |
| 9,138,187 B2 * | 9/2015 | Sharkey | A61B 5/4514 | |
| 9,220,554 B2 * | 12/2015 | O'Halloran | A61B 17/1671 | |
| 9,320,422 B1 * | 4/2016 | Makhlouf | A61B 1/00094 | |
| 9,339,294 B2 * | 5/2016 | Mandeen | A61B 17/3472 | |
| 9,522,001 B2 * | 12/2016 | Bui | A61B 50/33 | |
| 9,532,883 B2 * | 1/2017 | McLuen | A61F 2/441 | |
| 9,730,707 B2 * | 8/2017 | Sasaki | A61B 17/8852 | |
| 10,265,099 B2 * | 4/2019 | Pellegrino | A61B 18/1815 | |
| 2002/0013514 A1 * | 1/2002 | Brau | A61B 17/02 | 600/213 |
| 2003/0073998 A1 * | 4/2003 | Pagliuca | A61B 17/0293 | 606/86 A |
| 2004/0078079 A1 * | 4/2004 | Foley | A61B 17/025 | 623/17.11 |
| 2004/0186356 A1 * | 9/2004 | O'Malley | A61B 17/0293 | 600/231 |
| 2005/0004593 A1 * | 1/2005 | Simonson | A61B 17/025 | 606/191 |
| 2005/0075578 A1 * | 4/2005 | Gharib | A61B 5/6828 | 600/546 |
| 2005/0203345 A1 * | 9/2005 | Yamaguchi | A61B 17/025 | 600/204 |
| 2006/0211953 A1 * | 9/2006 | Zannis | A61B 90/06 | 600/587 |
| 2007/0179340 A1 * | 8/2007 | Jorgensen | A61B 1/04 | 600/139 |
| 2008/0249481 A1 * | 10/2008 | Crainich | A61B 17/1642 | 604/264 |
| 2008/0281364 A1 * | 11/2008 | Chirico | A61B 17/8819 | 606/86 A |
| 2009/0076551 A1 * | 3/2009 | Petersen | A61B 17/1757 | 606/247 |
| 2009/0156903 A1 * | 6/2009 | Guederian | A61B 17/02 | 600/204 |
| 2010/0069974 A1 * | 3/2010 | Oren | A61B 17/1778 | 606/86 R |
| 2010/0076502 A1 * | 3/2010 | Guyer | A61F 2/4611 | 606/86 R |
| 2011/0046446 A1 * | 2/2011 | Hirayama | A61B 1/05 | 600/158 |
| 2011/0106124 A1 * | 5/2011 | Beauchamp | A61B 17/1642 | 606/170 |
| 2013/0012946 A1 * | 1/2013 | Janssens | A61B 17/17 | 606/80 |
| 2013/0267892 A1 * | 10/2013 | Woolford | A61M 3/0216 | 604/34 |
| 2014/0088368 A1 * | 3/2014 | Park | A61B 17/0218 | 600/204 |
| 2015/0060462 A1 * | 3/2015 | Colbert | A61M 5/002 | 220/553 |
| 2016/0045334 A1 * | 2/2016 | Ries | A61F 2/447 | 623/17.16 |
| 2017/0196508 A1 * | 7/2017 | Hunter | A61B 5/036 | |
| 2017/0332886 A1 * | 11/2017 | Choi | A61B 1/3135 | |
| 2018/0008126 A1 * | 1/2018 | Arai | A61B 1/015 | |
| 2018/0028703 A1 * | 2/2018 | McLaughlin | B65D 1/38 | |
| 2018/0271574 A1 * | 9/2018 | Ammerman | A61B 17/1757 | |
| 2018/0333222 A1 * | 11/2018 | Sauer | A61B 50/30 | |

* cited by examiner

SURGICAL INSTRUMENT SET FOR USE DURING UNILATERAL BIPORTAL ENDOSCOPY

CROSS REFERENCE TO RELATED APPLICATION

The present application claims priority to Korean Patent Application Nos. 10-2017-0151636 and 10-2018-0008451, filed on Nov. 14, 2017 and Jan. 23, 2018 respectively, the entire contents of which is incorporated herein for all purposes by this reference.

BACKGROUND OF THE INVENTION

Field of the Invention

The present invention relates generally to a method of unilateral biportal endoscopy and a surgical instrument set used in the same. More particularly, the present invention relates to a method of unilateral biportal endoscopy which separately secures a working portal for surgical instruments and an endoscopic portal for an endoscope, thereby providing a more accurate spinal surgery, and to a surgical instrument set which can be effectively applied to the method.

Description of the Related Art

The human spine consists of seven cervical vertebrae, twelve thoracic vertebrae, five lumbar vertebrae, the sacrum formed of five fused sacral vertebrae, and the coccyx formed of four fused coccygeal vertebrae. Each vertebra is connected to an adjacent vertebra by a set of joints, and there is an intervertebral disc between each vertebra.

The intervertebral disc lies between adjacent vertebrae and functions to absorb and distribute the loads of the body and impact, as well as functioning to hold the vertebrae together, and functioning to separate the vertebrae from each other such that the size of the intervertebral foramen is maintained and thus the spinal nerve is not compressed.

When the intervertebral disc is deformed or ruptured and herniates from its normal position, or when the facet joint is damaged or degenerated, or when the vertebrae are deformed and displaced from their normal positions, the nerves passing through the spinal carnal are compressed, causing pain.

Meanwhile, as a surgical procedure for performing the above-described spinal disease, a conventional incision is a method of making a large incision in a surgical site. Thus, the conventional incision has a high probability of damaging the blood vessels as well as the spinal nerves and muscles, causes a large amount of bleeding, and has a long recovery period.

In order to solve such a problem, recently, percutaneous stenoscopic lumbar decompression (PSLD), which is a minimally invasive spinal surgical method, has been performed. However, the PSLD itself is a challenging procedure, and an operator may suffer from technical difficulties due to a restricted field of vision despite using a microscope or spinal endoscope as a supplementary device.

On the other hand, nerve branches entrapped by fibrous adhesion can be treated to some degree by only epidural block or epidural neurolysis in the stage of weak adhesions or mild stenosis.

However, when the adhesion or stenosis is severe, approach to the intervertebral foramen is difficult with the procedure described above, or even when treatment is performed after approaching to the intervertebral foramen, there is a high possibility that the pain will recur as a treated area becomes clogged again.

There is percutaneous foraminotomy as the most effective treatment method that can be applied in such circumstances. Percutaneous foraminotomy is a surgical procedure whereby an enlarging device is directly inserted into the intervertebral foramen through the patient's skin, and adhesions or bone spurs compressing nerve branches exiting the intervertebral foramen are removed and thus the pain is resolved, thereby relieving the compression applied to the blood vessels in the intervertebral foramen and improving the blood flow around nerves.

For such percutaneous foramnotomy, Korean Patent No. 10-1302453 entitled "percutaneous extraforaminotomy with foraminal ligament resection and instrument tools being used for the same" is disclosed.

A surgical method and a surgical instrument introduced in the document of the related art is used for securing a single pathway extending to a surgical site and expanding the intervertebral foramen by removing fibrous adhesion, etc. which block the intervertebral foramen, and is configured such that a trocar and a cannula that secure a pathway extending to a target point, an end mill passing through a guide hole of the cannula and having at an end thereof a blade tip, and a curette having a scraping tip inserted into the guide hole and scraping tissue inside the intervertebral foramen.

However, since the conventional surgical method is performed through a single pathway, a field of vision is poor and operability of the surgical instruments is poor as well. For example, due to a momentary mistake, the blade tip may severely damage normal tissue or touch the blood vessels, causing internal bleeding. Moreover, the surgical instrument is also problematic in that a structure thereof is simple and thus operative effects other than detaching tissue at a target point and scrapping the detached tissue may not occur.

SUMMARY OF THE INVENTION

Accordingly, the present invention has been made keeping in mind the above problems occurring in the related art, and the present invention provides a method of unilateral biportal endoscopy, which is capable of securing a clear field of vision, thereby enabling accurate identification and removal of lesion and securing high safety. In addition, the method enables minimum invasion with fewer scars and less risk of muscle damage, bleeding, and infection, thereby achieving a rapid therapeutic effect.

Further, the present invention provides a surgical instrument set used in unilateral biportal endoscopy, which includes a plurality of instruments ergonomically designed to be suitable for each process step in spine surgery, thereby enabling a more efficient surgery.

In order to achieve the above object, according to one aspect of the present invention, there is provided a method of unilateral biportal endoscopy, the method including: firstly securing pathways for a working portal and an endoscopic portal that extend toward a surgical site in the body of a patient and are distanced from each other; secondarily securing a pathway of additionally securing an access pathway for a surgical instrument and a working space by retracting the muscle inside the secured working portal; inserting the surgical instrument required for surgery into the pathways secured by the firstly and secondarily securing the pathways; inserting an endoscope into the endoscopic portal; performing surgery using the surgical instrument inserted into the working portal while monitoring the surgical site through the endoscope; removing the surgical instrument and the endoscope after the performing the surgery; and suturing entrances of the working portal and the endoscopic portal.

The firstly securing the pathways may include: marking positions of the entrances of the working portal and the endoscopic portal on the skin of the patient; incising marking portions marked by the marking; inserting an enlarging tube into the body through an incision opened by the incising, thereby forming a pathway extending toward the surgical site; and enlarging the pathway to enlarge a diameter of the pathway by using enlarging tubes having different sizes.

The secondarily securing the pathway may include: detaching the muscle from the bone at the surgical site; and retracting the muscle detached from the bone through the detaching the muscle and securing the working space.

The method may further include: supplying a saline solution from outside to the surgical site and discharging materials generated at the surgical site from the body, during the performing the surgery.

The working portal and the endoscopic portal may be configured such that the entrances thereof are distanced from each other, and the portals may extend into the body to be close to each other such that ends thereof meet with each other at the surgical site.

According to another aspect of the present invention, there is provided a surgical instrument set used in unilateral biportal endoscopy, the surgical instrument set including: a plurality of enlarging tubes having different diameters and configured to form two separate passageways including a working portal and an endoscopic portal that extend to a surgical site for progression of bidirectional vertebral endoscopic surgery; a muscle detacher detaching the muscle from the bone at the surgical site by being inserted into one of the pathways secured by the enlarging tubes; a muscle retractor retracting the muscle separated from the bone by the muscle detacher and securing an additional working space; and an endoscope inserted into the body through a remaining one of the pathways secured by the enlarging tubes and capturing an image of the surgical site.

The surgical instrument set may further include a double ended retractor inserted into a space created by the muscle detacher and detaching the nerve root from the bone or ligamentum flavum, the double ended retractor being selectively used during the unilateral biportal endoscopic surgery.

The surgical instrument set may further include: as an instrument for use when an artificial disc is required to be inserted into a disc space during the unilateral biportal endoscopic surgery, a bone chip cannula provided with a collecting portion collecting and concentrating bone chips supplied from outside, and a guide tube portion connected to the collecting portion and extending in a lengthwise direction thereof, the guide tube portion guiding the bone chips to the disc in a state of reaching the surgical site through one of the pathways; and a bone chip impactor impacting on the bone chips guided to the disc space such that the bone chips are seated in the disc.

The surgical instrument set may further include any one of: a radiofrequency probe heating and removing a target tissue to be removed located at the surgical site after reaching the surgical site in the body through the working portal secured by the enlarging tubes; a K-punch physically detaching and removing the target tissue to be removed after reaching the surgical site in the body through the working portal; and a round drill grinding necessary bone located at the surgical site after reaching the surgical site in the body through the working portal.

The radiofrequency probe may include: an insertion rod inserted into the body through the working portal so as to reach the surgical site; an electrode tip provided at a front end of the insertion rod and outputting radiofrequency heat by being applied with electric power from outside; and a safety protrusion formed on a surface of the electrode tip and separating the surface of the electrode tip from tissue to prevent thermal damage thereto.

The K-punch may include: an entry rod inserted into the body through the working portal so as to reach the surgical site and provided at a front end thereof with a retaining step portion; a slider slidably engaged with the entry rod and moving forward and backward with respect to the retaining step portion; a rotary shaft fixed to a rear side of the entry rod and rotated by manipulation of an operator to control a direction of the retaining step portion; a pushing rod fixed at a front end thereof to the slider and extending from a rear end thereof to a rear side of the rotary shaft; and a handle portion moving the pushing rod forward such that the slider is pressed and moved toward the retaining step portion.

The round drill may include: an outer tube having a predetermined diameter and extending in a lengthwise direction thereof, the outer tube reaching the surgical site through one of the pathways and having an inclined opening inclined at a front end thereof to have an acute angle with respect to the lengthwise direction of the outer tube; a tube holder fixed to a rear end of the outer tube; and a drill body including a burr exposed to outside of the outer tube and on which diamond powder is distributed.

The endoscope may be provided with: a hollow tube-shaped guide tube extending in a direction thereof so as to reach at a first end thereof the surgical site in the body through the remaining one of the pathways during use, the guide tube accommodating a probe of an endoscope camera; a saline solution guiding portion provided at a rear end of the guide tube and guiding a saline solution injected from outside into the guide tube, the saline solution guiding portion including a valve body fixed to the rear end of the guide tube and allowing the saline solution injected through an inlet to pass therethrough and move to the guide tube, and a flow control valve provided at the valve body and controlling the saline solution passing through the valve body; and an adapter portion provided at the rear end of the guide tube and guiding the probe of the endoscope camera to the guide tube.

A damping chamber may be provided between the valve body and the guide tube, the damping chamber receiving and storing the saline solution passing through the valve body and guiding the saline solution to the guide tube.

A plurality of valve bodies may be provided on an outer circumferential surface of the damping chamber such that a supply amount of the saline solution to the damping chamber is increased.

The guide tube may be provided on an inner circumferential surface thereof with a linear guide groove extending in the lengthwise direction of the guide tube and guiding the saline solution introduced in the guide tube in the lengthwise direction of the guide tube, such that the saline solution reaches a lens provided at a front end of the probe of the endoscope camera.

A plurality of linear guide grooves is arranged on the inner circumferential surface of the guide tube in a circumferential direction thereof, wherein a supporting protrusion may be provided between each linear guide groove and an adjacent linear guide groove, the supporting protrusion being in contact with the probe of the endoscope camera.

The guide tube may be provided at a front end thereof with a projecting portion and a depressed portion that are repeatedly provided in a wave pattern in a circumferential direction of the guide tube and guide the saline solution discharged from the guide tube to flow out in a radial direction of the guide tube.

The guide tube may be provided with a side slit formed on a side of a front end of the guide tube and discharging the saline solution discharged from the guide tube to a side of the guide tube.

In the present invention, the method of unilateral biportal endoscopy is capable of securing a clear field of vision, thereby enabling accurate identification and removal of a lesion and securing high safety. In addition, the method enables minimal incision with fewer scars and less risk of muscle damage, bleeding, and infection, thereby achieving a rapid therapeutic effect.

Further, in the present invention, the surgical instrument set used in unilateral biportal endoscopy includes a plurality of instruments ergonomically designed to be suitable for each process step in spine surgery, thereby enabling a more efficient surgery.

DETAILED DESCRIPTION OF THE INVENTION

Figure 1:
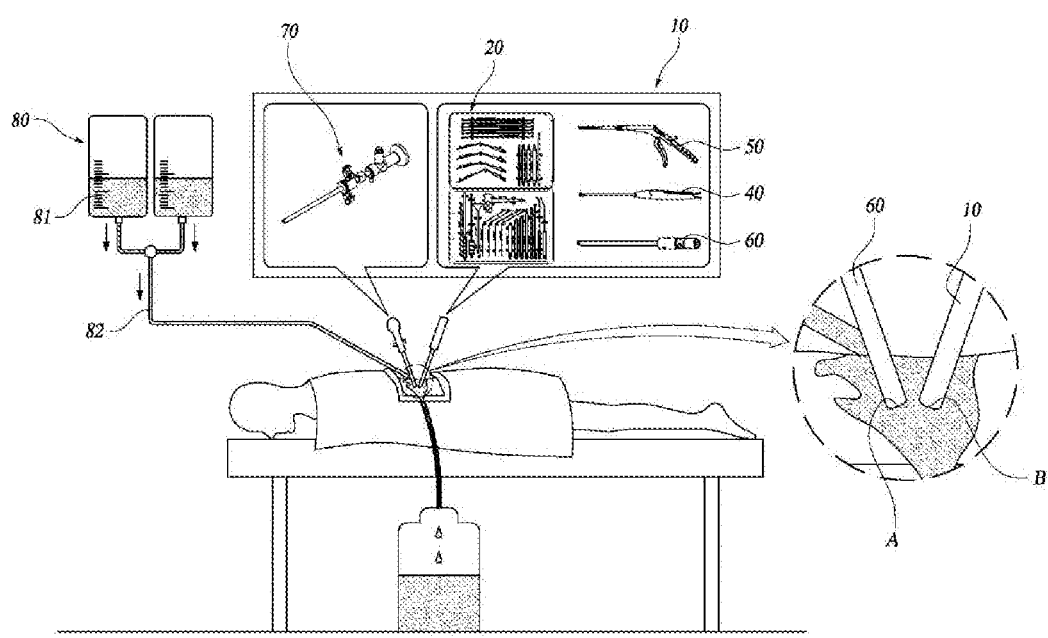
FIG. 1 is a view showing a basic concept of a method of unilateral biportal endoscopy.

Hereinbelow, an exemplary embodiment of the present invention will be described in detail with reference to the accompanying drawings. Throughout the drawings, the same reference numerals will refer to the same or like parts.

FIG. 1 is a view showing a basic concept of a method of unilateral biportal endoscopy.

The method of unilateral biportal endoscopy is a method whereby two pathways, that is, an endoscopic portal A and a working portal B perforate a surgical site, a surgical instrument set 10 is inserted through the working portal B while an endoscope 70 is inserted through the endoscopic portal A, thereby treating the surgical site. In some cases, the surgical instrument may be inserted through the endoscopic portal A while the endoscope 70 may be inserted through the working portal B.

In particular, a saline solution 81 is injected through the endoscope 70 such that the saline solution is guided to flow through the surgical site, thereby allowing the saline solution to remove residues from the surgical site. The used saline solution is discharged from the body through of the working portal B. As will be described later, the endoscope 70 according to the present embodiment functions to visualize an internal surgical site, as well as to guide the saline solution into the body.

The unilateral biportal endoscopy is characterized in that the surgical instrument and the endoscope approach the surgical site through different pathways, so that a clear field of vision is obtained compared to a conventional method of forming a single incision. Having a clear field of vision is very important factor in spinal surgery.

In addition, since the surgical instrument does not share a pathway with the endoscope 70, a motion of the surgical instrument is relatively free within the pathway, thereby enabling a more efficient surgery.

The surgical instrument set 10 has a very wide range and includes a tool kit 20 including various types of small tools, a radiofrequency probe 40, a K-punch 50, a round drill 60, and the endoscopes 70. The components of the surgical instrument set 10 are selectively used in accordance with the progress of unilateral biportal endoscopic surgery, and all are ergonomically designed.

Figure 2A:
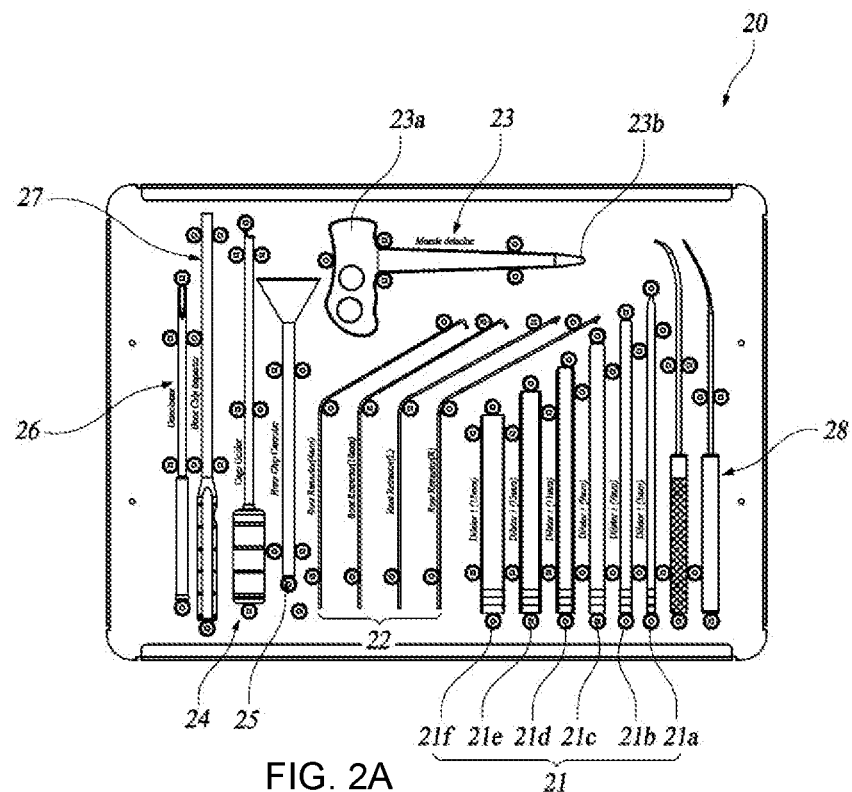
FIGS. 2A and 2B are views showing a tool kit shown in FIG. 1.
Figure 2B:
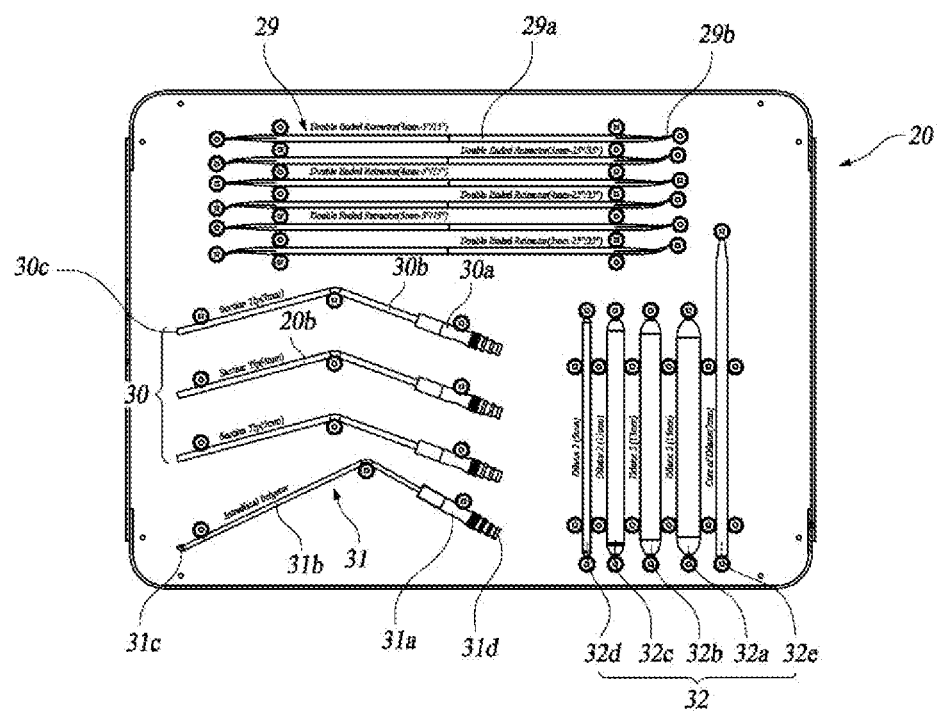
Figure 3A:
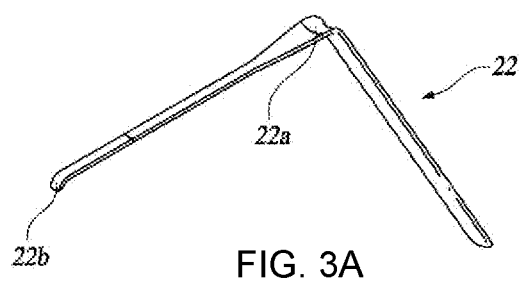
FIGS. 3A to 3D are perspective views showing a root retractor shown in FIG. 2A.
Figure 3B:
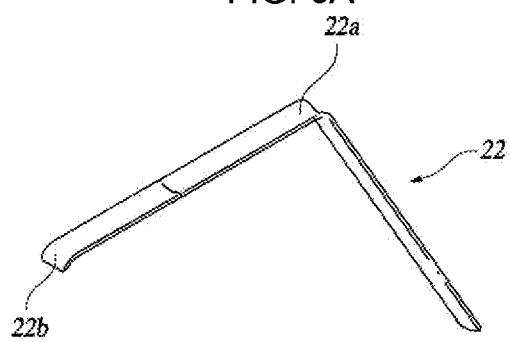
Figure 3C:
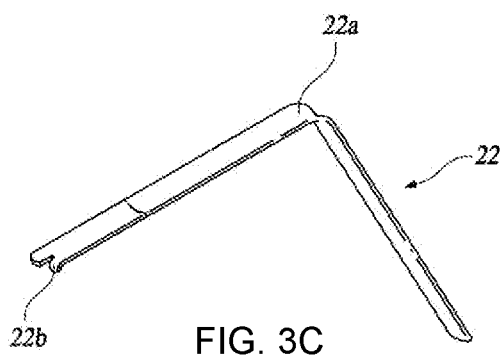
Figure 3D:
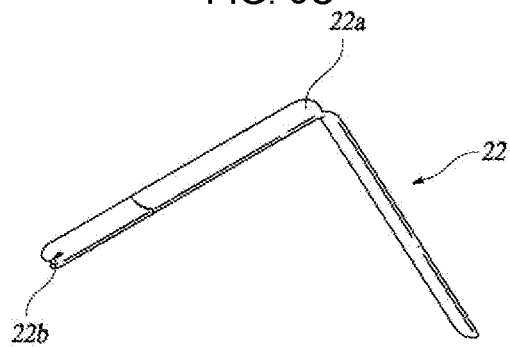
Figure 4:
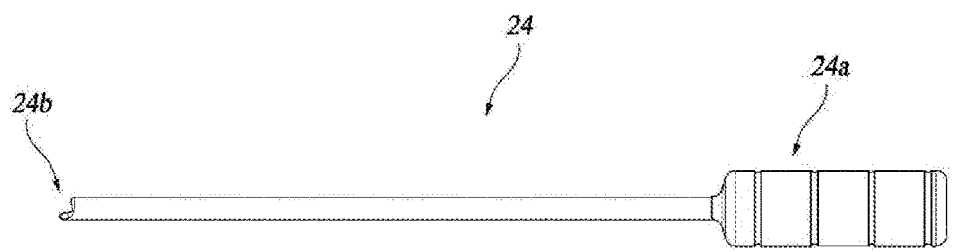
FIG. 4 is a view showing a cage guider shown in FIG. 2A.
Figure 5:
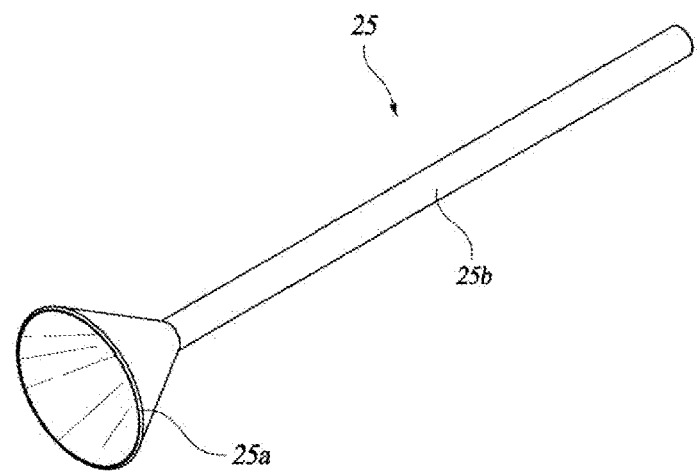
FIG. 5 is a perspective view showing a bone chip cannula shown in FIG. 2A.
Figure 6:
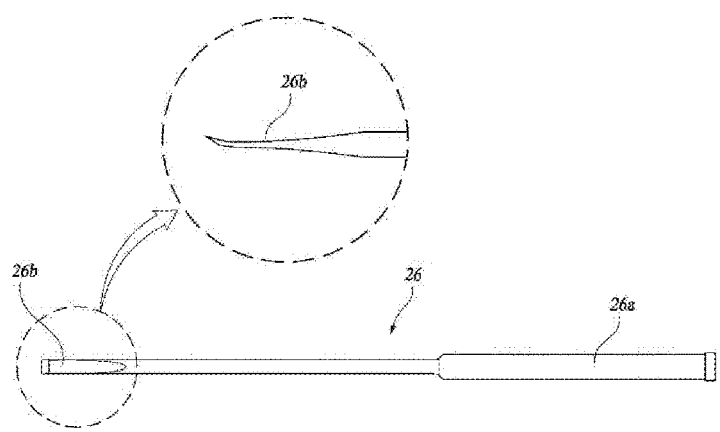
FIG. 6 is a view showing an osteotome shown in FIG. 2A.
Figure 7:
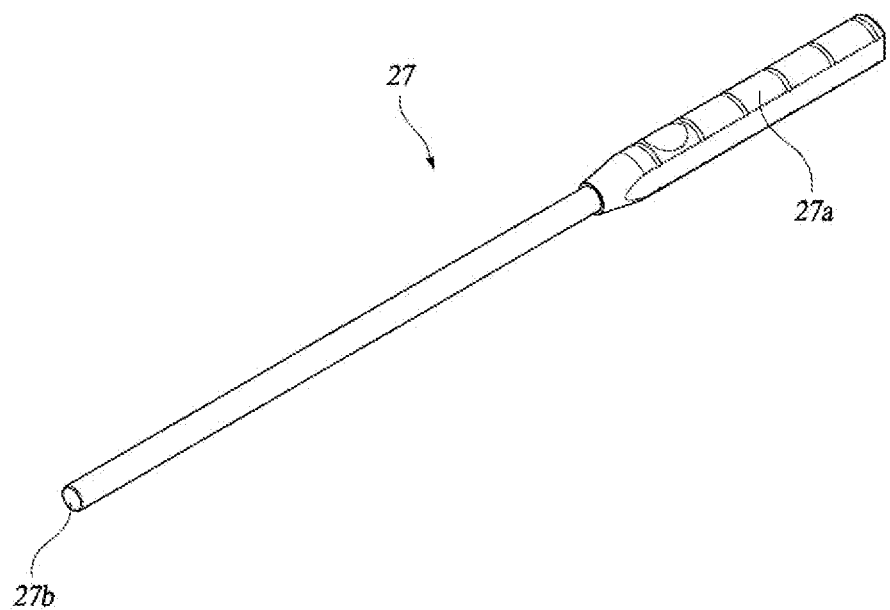
FIG. 7 is a perspective view showing a bone chip impactor shown in FIG. 2A.

FIGS. 2a and 2b are views showing the tool kit shown in FIG. 1, and FIGS. 3a to 3d are perspective views showing a root retractor 22 shown in FIG. 2a. Further, FIGS. 4 to 8 are views showing the surgical instruments included in the tool kit 20.

As shown in the drawings, the tool kit 20 includes an enlarging tube 21 for enlarging the size of the working portal B and a dilator 32 for retaining the enlarged working portal B.

The enlarging tube 21 is an instrument for enlarging the working portal B by being sequentially inserted thereinto by size in order to secure space for allowing entry of other surgical instruments to the working portal B formed at a surgical site during the unilateral biportal endoscopic surgery. In other words, after making a minimal incision in the skin with a scalpel, the enlarging tubes are stepwisely inserted into the incision to enlarge the same.

The enlarging tube 21 has a hollow tube shape having different diameters and lengths. In the present embodiment, the enlarging tube 21 is provided as six types ranging from a first enlarging tube 21a to a sixth enlarging tube 21f having different sizes. The first to sixth enlarging tubes 21a to 21f are selectively used as required.

The enlarging tube 21 may be provided on the outer circumferential surface thereof with a scale (not shown) marked to indicate the depth of insertion. The first enlarging tube 21a has a sharp front end and serves to enlarge the working portal B and the endoscopic portal A immediately after incision with a scalpel.

The dilator 32 is a bar instrument inserted into the working portal B to retain the working portal B secured by the enlarging tube 21. The dilator 32 includes a first dilator 32a, a second dilator 32b, a third dilator 32c, and a fourth dilator 32d having different sizes as shown in the drawing.

A dilator core 32e is used to enlarge the working portal B and the endoscopic portal A immediately after incision with a scalpel.

In addition, the tool kit 20 further includes a muscle detacher 23, a double ended retractor 29, a root retractor 22, a suction tip 30, an intradiscal irrigator 31, a cage guider 24, a bone chip cannula 25, an osteotome 26, a bone chip impactor 27, and an end plate remover 28.

The muscle detacher 23 is an instrument for securing an access pathway for an instrument used in the subsequent operation and a working space by detaching muscles from bones at a surgical site in a state of being inserted into the secured incision. In other words, the muscle detacher 23 is inserted between the muscle fibers of the fine muscle rather than cutting the muscle. The muscle detacher 23 has a blade portion 23b and a handle portion 23a. The blade portion 23b has a soft round shape to minimize the skin wound at the surgical site.

The double ended retractor 29 is an instrument being inserted in the working space created by the muscle detacher 23 to detach the nerve root from the bone or the ligamentum flavum or to detach the muscle or ligament.

The double ended retractor 29 is configured such that the angle of tip portions 29b provided at opposite ends thereof are variable, thereby being used for detaching and removing risk factors near the nerves or applying bone wax to a bleeding point during bone bleeding. The tip portion 29b is configured such that an angle thereof is in a range of 5 to 25 degrees, and a width varies to 5.5 mm/4 mm/3 mm. The angle and width of the tip 29b may vary.

The double ended retractor 29 is provided at a center thereof with a handle portion 29a. The handle portion 29a may be provided with a recessed groove for preventing the operator's fingers from slipping or an uneven portion having a predetermined pattern for increasing friction.

The root retractor 22 is an instrument for securing a working space and a constant water pressure in the working space by retracting the muscle and providing a pathway that guides the surgical instruments to be inserted and removed therethrough. As shown in FIGS. 3a to 3d, the root retractor 22 is provided at a center thereof with a first curved portion 22a, and at an end thereof with a second curved portion 22b.

The first curved portion 22a has a curve angle of about 120 degrees, which is an ergonomically and mechanically ideal angle formed between the surgical instrument inserted and a lesion. In addition, the outer edge of the first curved portion 22a has a semi-tubular shape, and the second curved portion 22b has a shape curved in the same direction as the first curved portion 22a or has a half-curved shape to hold the muscle to the nerve root.

The opposite side of the semi-tubular shaped outer edge of the root retractor 22 may serve as the pathway for insertion or removal of the surgical instruments, which detaches soft tissue such as ligaments, etc., or resects or inserts a disc.

The root retractor 22 may have a width of 4 mm/10 mm and the root retractor having a suitable size suitable according to a surgical site may be selectively used. The root retractor 22 helps to open and close the working portal B and maintains the working space and water pressure such that an operator can see clear images of the surgical site. In addition, the root retractor 22 serves to control compression and decompression of the nerve root to enable efficient surgery without damaging the nerve root.

The suction tip 30 is an instrument for sucking a saline solution injected for surgery or the soft tissue as well as tissue debris generated during surgery. During unilateral biportal endoscopic surgery, a constant pressure is required within the body, and thus a constant pressure (e.g., 30 to 50 mmHg) is maintained using the suction tip 30. The suction tip 30 can prevent poor visibility of the surgical field from being caused due to the bone, the tissue debris, etc. during surgery.

The suction tip 30 includes a handle portion 30a to which an outlet is connected and a curve-shaped suction pipe portion 30b having at a front end thereof a suction hole 30c. The suction pipe portion 30b may be configured such that a curve angle thereof is about 130 to 150 degrees, and a diameter thereof is 3 to 5 mm.

The suction tip 30 may be used for removing residue, etc. after a space for inserting artificial disc into a disc space is created, or may be used for checking a bleeding site by suctioning a bleeding portion in the peripheral corner of the disc in addition to the disc space.

The suction tip 30 can allow the surrounding debris to be discharged before and after insertion of the artificial disc without remaining within the body, and allow the washing area to be accurately ascertained while providing a sufficient field of vision, thereby enabling quick washing and washing water saving.

The intradiscal irrigator 31 includes a handle portion 31a having a wash water inlet 31d, and a water tube portion 31b curved at a predetermined angle to secure a field of vision of an operator and having at a front end thereof a discharge hole 31c. The water tube portion 31b has a curve angle of about 111 to 130 degrees. When the curve angle is less than 111 degrees, the operator's field of vision is obstructed. Additionally, when the curve angle is greater than 130 degrees, the operator's gaze must be lowered to see the discharge hole 31c.

The cage guider 24 is an instrument for seating a cage (not shown) in the disc space. The cage guider 24 is provided at a first end thereof with a carrying portion 24b on which the cage is placed, and at a second end thereof with a handle portion 24a.

The bone chip cannula 25 is an instrument for collecting the bone chips and inserting them into the cage. The bone chip cannula 25 includes a funnel-shaped collecting portion 25a for concentrating and collecting the bone chips supplied from the outside, and a guide tube portion 25b connected to the collecting portion 25a and extending in the lengthwise direction thereof, the guide tube portion 25b guiding the bone chips to the disc in a state of reaching a surgical site.

The osteotome 26 is an instrument for cutting unnecessary bones during surgery. The osteotome 26 is provided at a front end thereof with a cutting blade portion 26b cutting the bone, and at an opposite end to the tip end thereof with a handle portion 26a.

The bone chip impactor 27 is an instrument for impacting on the artificial disc inserted into the disc space or the collected bone material so as to be seated in a precise position. The bone chip impactor 27 is provided at a front end thereof with a tip portion 27b being in contact with a target to be impacted thereon, and at an opposite end to the tip end thereof with a handle portion 27a.

Figure 8A:
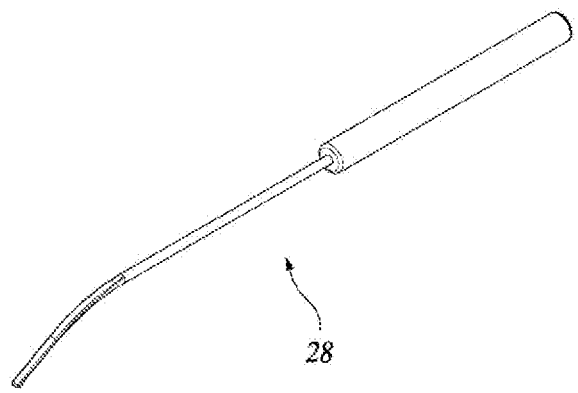
FIGS. 8A to 8C are views showing an end plate remover shown in FIG. 2A.
Figure 8B:
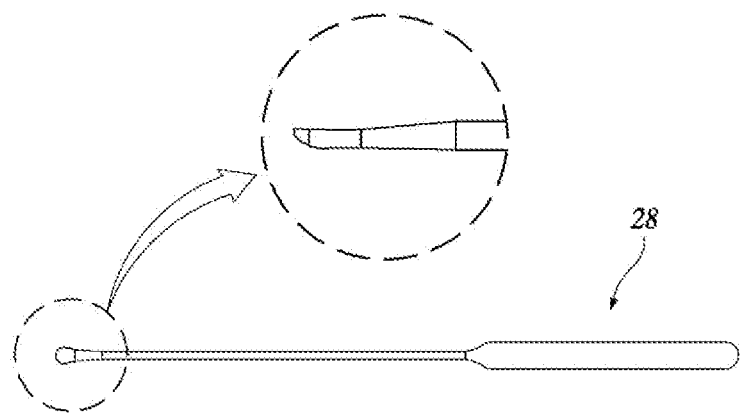
Figure 8C:
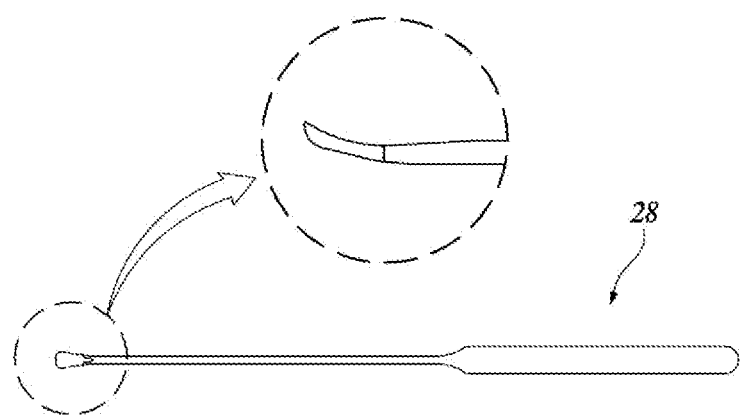

Further, the end plate remover 28 is an instrument for removing the end plate located between the vertebrae and the disc, and is curved at a front end thereof in a hook shape. Since the tip end of the curved end plate remover 28 has a hook shape, each approach to and removal of the end plate located between the vertebrae and the disc is possible. As shown in FIGS. 8a, 8b, and 8c, the tip end of the end plate remover 28 may vary in shape.

Figure 9:
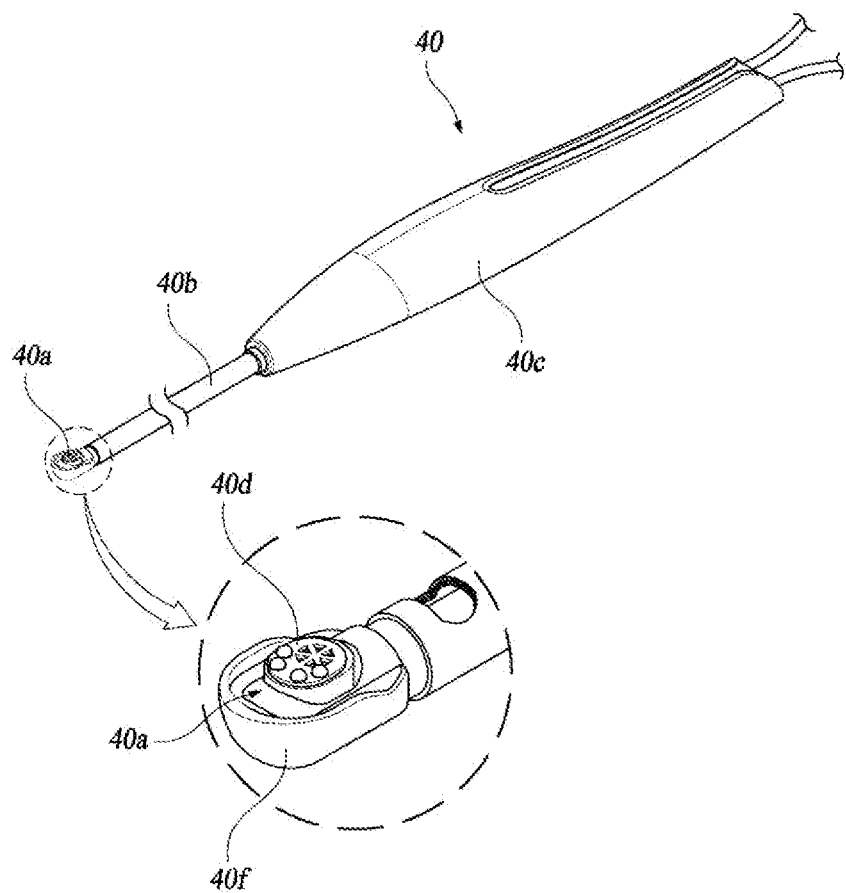
FIG. 9 is a partial perspective view showing a radiofrequency probe shown in FIG. 1.

FIG. 9 is a partial perspective view showing the radio frequency probe 40 shown in FIG. 1.

The radiofrequency probe 40 is an instrument for heating and removing the soft tissue, disc, epidural fat, and ligaments. While a conventional radiofrequency probe is problematic in that a tip thereof where radiofrequency is generated is in direct contact with a surgical site and thus the surrounding nerve is damaged, the radiofrequency probe 40 according to the present invention has a safety protrusion (not shown) whereby no damage to normal tissue is caused.

The radiofrequency probe 40 includes an insertion rod 40b inserted into the body so as to reach a surgical site, an electrode tip 40a provided at a front end of the insertion rod 40b and outputting radiofrequency heat by being applied with electric power from outside, and the safety protrusion formed on the surface of the electrode tip 40a and separating the surface of the electrode tip 40a from the body tissue to prevent thermal damage.

In addition, the radiofrequency probe 40 may further include an electric power wire supplying electric power to the radiofrequency probe 40, and a discharge tube extending from the outside of a casing 40c and discharging a saline solution in the body therefrom.

Moreover, the electrode tip 40a may be detachably fitted into the insertion rod 40b and includes a shield portion 40f. The shield portion 40f is a soft round-shaped member for minimizing damage to the body tissue and facilitating insertion when the electrode tip 40a is inserted into the body. The shield portion 40f also serves to block heat of plasma from being transferred to normal tissue.

Figure 10:
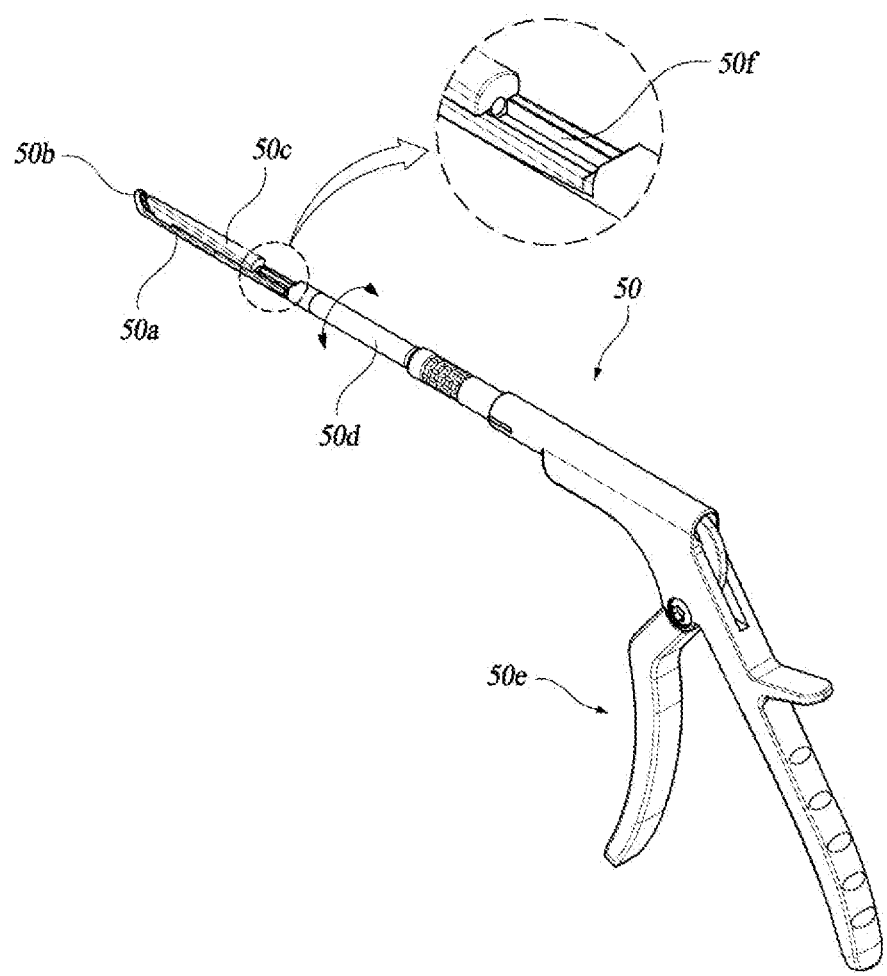
FIG. 10 is a perspective view showing a K-punch shown in FIG. 1.

FIG. 10 is a perspective view showing the K-punch 50 shown in FIG. 1.

The K-punch 50 is an instrument for detaching and removing the bone, ligamentum flavum, soft tissue, etc. and includes an entry rod 50a, a slider 50c, a rotary shaft 50d, a pushing rod 50f, and a handle portion 50e.

The entry rod 50a is a member being inserted into the body so as to reach a surgical site at a front end thereof, and is provided at the front end thereof with a retaining step portion 5b. Further, the slider 50c is slidably engaged with a side of the entry rod 50a and moves forward and backward with respect to the retaining step portion 50b. The slider 50c is pressed and moved to the retaining step portion 50b in a state in which a target to be removed is positioned between the retaining step portion 50b and the slider 50c, whereby the target to be removed is physically fixed.

The rotary shaft 50d is fixed to the rear side of the entry rod 50a, and is rotated by an operator's operation as required during surgery such that the direction of the retaining step portion 50b is controlled. As such, by provision of the rotary shaft 50d, the handle portion 50e is operable at a comfortable angle regardless of the position of tissue to be removed.

The pushing rod 50f is fixed at a front end thereof to the slider 50c and extends from a rear end thereof to the rear side of the rotary shaft 50d, the pushing rod being configured to move forward to press and move the slider 50c to the retaining step portion 50b when the handle portion 50e is manipulated.

Figure 11:
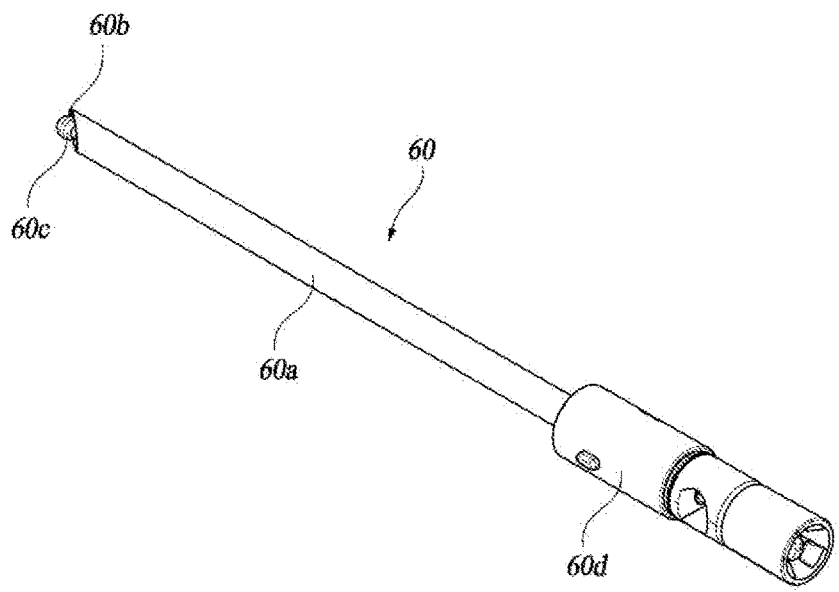
FIG. 11 is a perspective view showing a round drill shown in FIG. 1.

FIG. 11 is a perspective view showing a round drill 60 shown in FIG. 1.

The round drill 60 serves to grind unnecessary bone parts during surgery and is used in combination with a separate handpiece (not shown).

The round drill 60 is provided with an outer tube 60a having a predetermined diameter and extends in the lengthwise direction thereof, the outer tube 60a having an inclined opening 60b inclined at a front end thereof to form an acute angle (e.g., 38 degrees) with respect to the lengthwise direction of the outer tube 60a, a tube holder 60d fixed to a rear end of the outer tube 60a, and a burr 60c partially exposed to the outside of the outer tube 60a through the inclined opening 60b.

The inclined opening 60b is provided to partially cover the burr 60c such that the burr 60c removes only unnecessary portions without damaging normal tissue and the nerve.

The burr 60c is a cutting tip on which cutting diamond powder is distributed, and types thereof may vary. For example, a round burr, a diamond burr, etc. may be used. Unlike a conventional burr used in endoscopic surgery, the diamond burr is embedded with fine diamond powder. Since fine diamond powder is distributed to serve as a cutting blade, the depth of cutting the bone can be precisely controlled and bleeding can be minimized. In addition, the shape of the burr 60c may be implemented in other shapes such as a triangular pyramid shape as well as a round shape.

Figure 12:
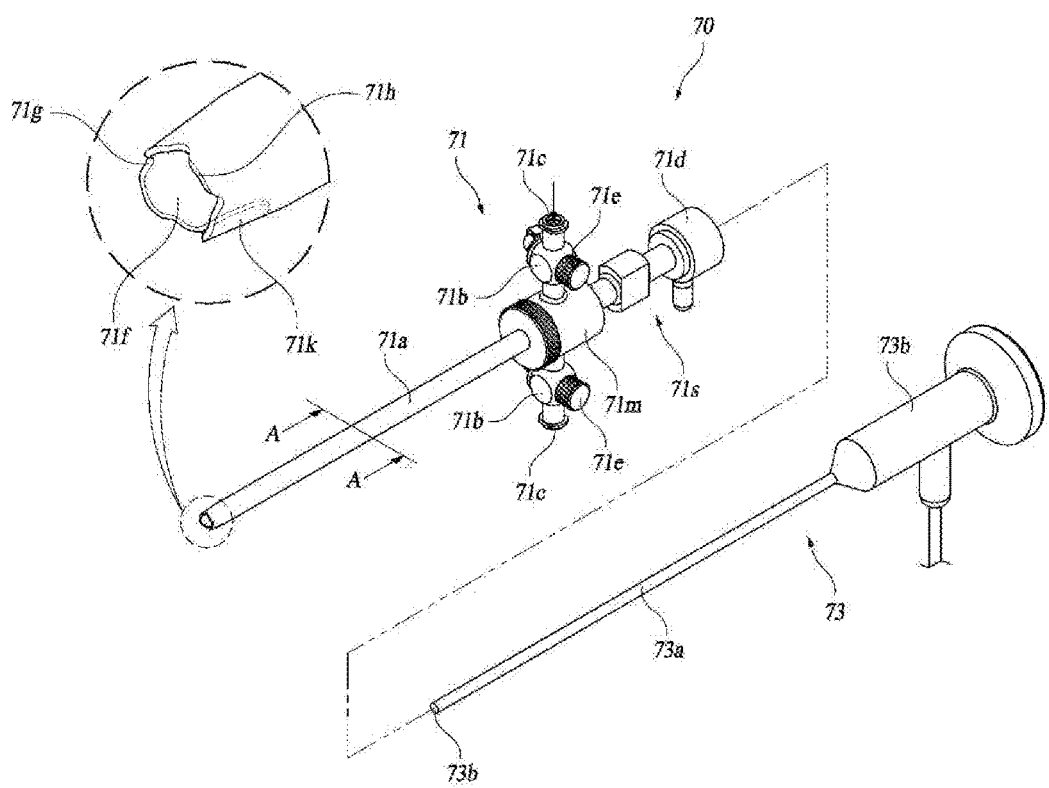
FIG. 12 is a perspective view showing an endoscope shown in FIG. 1.
Figure 13:
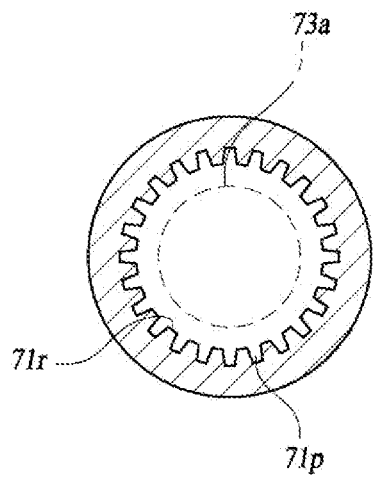
FIG. 13 is a cross-sectional view taken along line A-A of FIG. 12.
Figure 14:
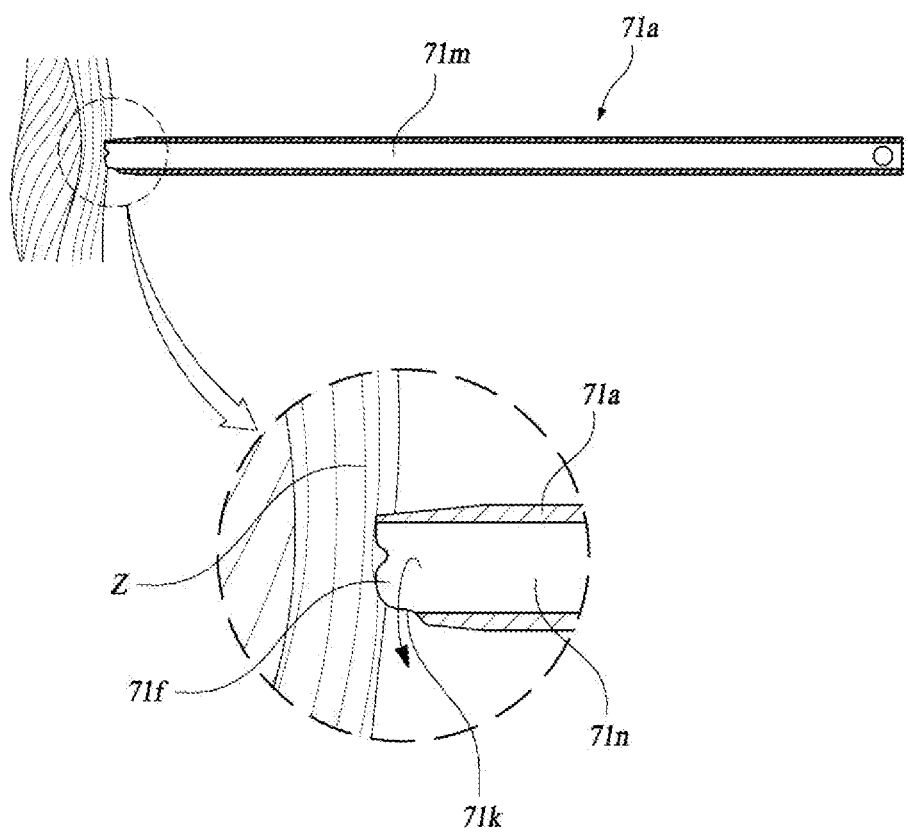
FIG. 14 is a sectional view showing a guide tube shown in FIG. 12.

FIG. 12 is a perspective view showing the endoscope 70 shown in FIG. 1, and FIG. 13 is a cross-sectional view taken along line A-A of FIG. 17. Further, FIG. 14 is a sectional view showing the guide tube 71a shown in FIG. 17. The endoscope 70 includes a sheath mechanism 71 and an endoscope camera 73.

The endoscope camera 73 is a device for identifying and capturing an image of a surgical site in the body, and includes a flexible probe 73a extending in the lengthwise direction thereof and having an optical fiber cable therein, A lens 73b provided at a front end of the probe 73a, and a lens barrel 73c provided at a rear end of the lens 73b.

The endoscope camera 73 may further include an imaging control device for capturing and recording images, a light source connected to a guide cable for illuminating a imaging site, the guide cable for transporting light to a distal end of the endoscope 70 for emitting light to the imaging site, and an endoscope tray storing the endoscope camera 73 and facilitating movement of the endoscope camera 73.

The sheath mechanism 71 is combined with the endoscope camera 73 to constitute a single endoscope 70 and serves to support the endoscope camera 73 during surgery whiling secure a field of vision. The reason why the sheath mechanism 71 is used is that the probe 73a of the endoscope camera is very thin and tends to be curved, and thus the lens 73b may not be allowed to reach a target point in the body. Another important function of the sheath mechanism 71 is to guide a saline solution to a target point.

The sheath mechanism 71 includes a guide tube 71a, a damping chamber 71m, a valve body 71b, and an adapter portion 71s.

The guide tube 71a is a hollow tube-shaped member that extends in the lengthwise direction thereof, and a first end thereof reaches a surgical site in the body when in use. The material of the guide tube 71a may vary and may be made of, for example, stainless steel or a synthetic resin including polypropylene.

The length of the guide tube 71a may vary as required. The guide tube 71a is inserted into the body through the portal secured by the enlarging tube 21.

In particular, the guide tube 71a is provided on an inner circumferential surface thereof with a plurality of guide grooves 71p. The guide grooves 71p extend in the lengthwise direction of the guide tube 71a and serve to guide a saline solution supplied from the outside to an outlet 71f.

As shown in FIG. 13, linear protrusions 71r are provided between the guide grooves 71p, respectively. The linear protrusions 71r are arranged in parallel with the guide grooves 71p, and a plurality of the protrusions are arranged in parallel to form the guide grooves 71p. The linear protrusions 71r and the guide grooves 71p are arranged in the circumferential direction of the guide tube 71a to be distanced from each other at predetermined intervals.

Additionally, the linear protrusions 71r are in partial contact with an outer circumferential surface of the probe 73a inserted into a space portion 71n of the guide tube 71a and to thereby support the probe 73a. The diameter of a virtual cylinder connecting the upper ends of the linear protrusions 71r is greater than the diameter of the probe 73a. Thus, the probe 73a can move vertically and horizontally in the space portion 71n and freely slide in the lengthwise direction thereof.

Furthermore, the guide tube 71a is provided at a front end thereof with a plurality of projecting portions 71h and a plurality of depressed portions 71g. The projecting portions 71h projects in a direction of the front end of the guide tube 71a, that is, in a direction in which a saline solution is discharged, and the depressed portions 71g are depressed in a direction opposite thereto. In particular, the projecting portions 71h and the depressed portions 71a are repeatedly provided in a wave pattern in the circumferential direction of the guide tube 71a.

The projecting portions 71h and the depressed portions 71a serve to guide a saline solution discharged from the guide tube 71a to flow out in the radial direction of the guide tube 71a. For example, when the front end of the guide tube 71a is clogged with the muscle, the saline solution is allowed to be supplied through the depressed portions 71a, or is imparted with directionality for securing a field of vision.

In addition, the guide tube 71a is provided with a side slit 71k formed on the side of the front end of the guide tube 71a. The side slit 71k serves to control the flow direction of a saline solution. In other words, during unilateral biportal endoscopic surgery, the flow direction of the saline solution is controlled, whereby the lens 73b is easily cleaned while the saline solution flows by gravity, thereby securing a field of vision of the endoscope 70.

The side slit 71k serves as a passage for a saline solution. For example, as mentioned above, the side slit 71k is provided to prevent a case where the depressed portions 71a of the guide tube 71a are clogged with tissue such as muscle Z and thus the saline solution is not efficiently discharged, and is provided to impart directionality to the saline solution to secure a field of vision.

The saline solution introduced into the guide tube 71a is discharged through the side slit 71k by gravity and washes away tissue or blood of the affected area, thereby securing a field of vision.

The adapter portion 71s serves to maintain a position of the endoscope camera 73 with respect to the sheath mechanism 71, and has a holder 71d for supporting the endoscope camera 73. The guide tube 71a is open at a rear end thereof to the rear side of the holder 71d. When the probe 73a is fully inserted into the guide tube 71a through the holder 71d, the endoscope camera 73 is supported by the holder 71d and thus is prevented from being separated backward.

Meanwhile, the damping chamber 71m is a space communicating with the rear end of the guide tube 71a, and serves to receive a saline solution supplied through an inlet 71c and a valve body 71b, store the same therein, and transfer the stored saline solution to the guide tube 71a.

By provision of the damping chamber 71m, deviation in the flow rate of a saline solution supplied to the guide tube 71a is kept as low as possible. When the damping chamber 71m is absent, a change in the flow rate of the saline solution supplied through a saline solution supply tube (reference numeral 82 in FIG. 1) is immediately reflected in the guide tube 71a. The capacity of the damping chamber 71m may vary as required.

Two valve bodies 71b are provided at the periphery of the damping chamber 71m, and each of the valve bodies 71 is provided with a flow control valve 71e. The flow control valve 71e serves to control the flow rate of a saline solution passing through the valve body 71b and is manipulated by an operator.

Reference numeral 71c denotes an inlet to which the saline solution supply tube 82 is connected. The saline solution having flowed through the saline solution supply tube 82 reaches the affected area through the inlet 71c via the valve body 71b, the damping chamber 71m, and the guide tube 71a.

Figure 15:
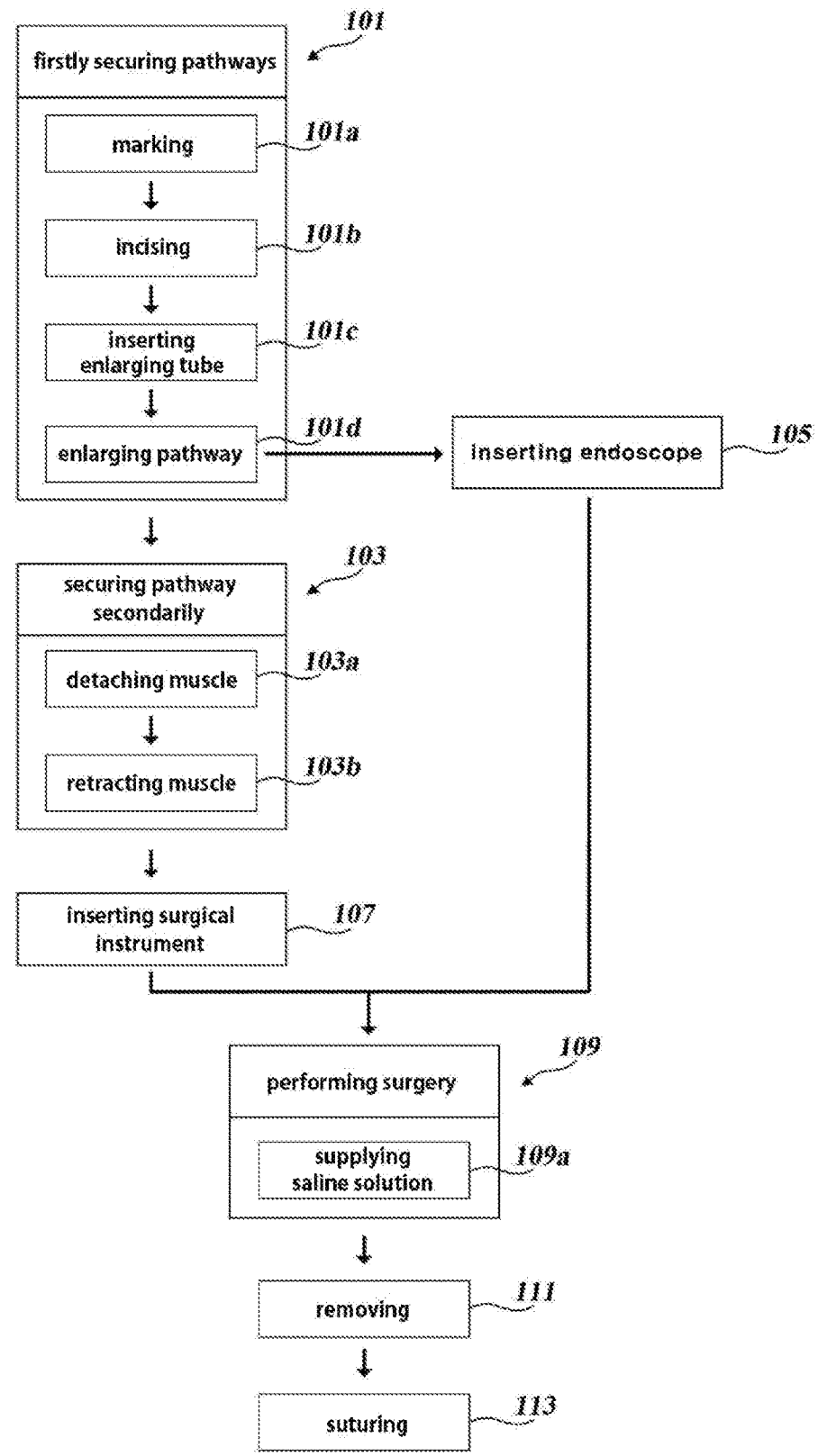
FIG. 15 is a block diagram showing the method of unilateral biportal endoscopy according to an embodiment of the present invention.

FIG. 15 is a block diagram showing the method of unilateral biportal endoscopy according to the embodiment of the present invention.

As shown in the drawing, the method of unilateral biportal endoscopy according to the present embodiment includes a step of firstly securing pathways S101, a step of secondarily securing a pathway S102, a step of inserting an endoscope S105, a step of inserting a surgical instrument S107, a step of performing surgery S109, a step of removing S111, and a step of suturing S113.

The step of firstly securing the pathways S101 is a process of forming two pathways extending toward a surgical site in the patient's body, that is, the working portal B and the endoscopic portal A, and includes marking S101a, incising S101b, enlarging tube inserting S101c, and pathway enlarging S101d.

First, the marking S101 is a process of marking points at which the working portal B and the endoscopic portal A are formed on the skin on the vertebral region of a patient lying in a prone position. In other words, entrances through which an instrument, such as the tool kit 20, the radiofrequency probe 40, the K-punch 50, or the round drill 60 from the surgical instrument set is inserted are marked. In particular, two marking points must be distanced from each other. The marking points vary depending on the location of a surgical site. When a lesion is located in a deep position, the distance between the two marking points is increased.

The working portal B and the endoscopic portal A are independent pathways to each other, and are configured to meet with each other at a lesion site in the body whereas the entrances thereof are separated from each other, thereby forming substantially sides of a triangle.

When the marking S101a is completed, the incising S101b is performed. For example, the incising S101b is a process of making incisions on marking portions using a scalpel, whereby the entrance through which the enlarging tube 21 is inserted is opened. Herein, the incision length may be about 5 mm.

Subsequently, the enlarging tube inserting S101c is a process of forming a straight pathway toward a surgical site by inserting the enlarging tube 21 into the body using the incision opened through the incising S101b as an entrance. Of course, the enlarging tube 21 used first is the first enlarging tube 21a having the smallest diameter.

The pathway enlarging S101d is a process of enlarging the diameter of the pathway by using enlarging tubes having different sizes. For example, in a state in which the first enlarging tube 21a is inserted into the body, the second enlarging tube 21b is inserted thereover and then the first enlarging tube 21a is taken out. Thereafter, the third enlarging tube 21c is inserted over the second enlarging tube 21c and then the second enlarging tube 21b is taken out in such a manner that the diameter of the pathway is increased.

The pathway enlarging S101d may be applied to both the endoscopic portal A and the working portal B. Needless to say, the diameter of the working portal B through which the surgical instrument set is inserted should be relatively large.

As described above, the endoscopic portal A and the working portal B formed through the step of firstly securing the pathways S101 are distanced from each other on the patient's epidermis but meet with each other at a surgical site in the body.

Subsequently, the step of secondarily securing the pathway S103 includes muscle detaching S103a and muscle retracting S103b. The muscle detaching S103a includes a process of detaching the muscle from the bone of a surgical site using the muscle detacher 23 described above. In other words, by inserting the muscle detacher 23 into the pathway secured through the step of firstly securing the pathways S101 to detach the bone and muscle of the surgical site, an access pathway for the instruments used in the subsequent operation and a working space is secured.

Further, the muscle retracting S103b is a process of securing an additional working space by retracting the muscle using the root retractor 22 described above. In other words, the muscle separated from the bone is retracted through the muscle detaching S103a, thereby securing a sufficient working space.

Subsequently, the step of inserting the surgical instrument S107 is a process of inserting the surgical instrument required for surgery through the working portal B secured through the step of secondarily securing the pathway S103. In other words, it is a process of inserting the required surgical instruments according to the progress of surgery. The radiofrequency probe 40, the K-punch 50, and the round drill 60 as well as the tool kit 20 are selectively inserted through the working portal B as required.

The step of inserting the endoscope S105 is a process of inserting the endoscope 70 through the secured endoscopic portal A. Of course, the sheath mechanism 71 and the lens 73b of the endoscope camera 73, which constitute the endoscope 70, must reach a lesion site.

Then, the step of performing the surgery S109 is performed. The step of performing the surgery S109 is a process of performing surgery using the surgical instrument inserted into the working portal B while monitoring a surgical site through the endoscope 70.

The step of performing the surgery S109 is a process of actually performing treatment on a surgical site to be treated in the body. As the treatment progresses, the required surgical instruments are inserted into the body through the working portal B. Of course, a surgery status is continuously monitored through the endoscope 70 during surgery.

In particular, during the step of performing the surgery S109, saline supplying S109a is performed. The saline supplying 109a is a process of supplying a saline solution supplied from the outside to a surgical site and discharging materials to be discharged generated during surgery from the body. As described above, the saline solution is guided through the guide tube 71a of the sheath mechanism 71. The injected saline solution allows debris at a surgical site and tissue removed to be discharged outside.

Subsequently, the step of removing S111 is a process of removing the used surgical instrument and the endoscope 70 from the body. Herein, the surgical instrument may be removed prior to removing the endoscope 70. For example, the endoscope camera 73 is used to check and identify a surgical site prior to removal thereof.

When the step of removing S111 is completed, the step of suturing S113 of suturing the entrances of the working portal B and the endoscopic portal A is performed, whereby surgery is completed.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A surgical instrument set used in unilateral biportal endoscopy, the surgical instrument set comprising:
   a plurality of enlarging tubes having different diameters and configured to form two separate passageways including a working portal and an endoscopic portal that extend to a surgical site for progression of bidirectional vertebral endoscopic surgery;
   a muscle detacher comprising a blade portion and a handle portion configured to detach a muscle from a bone at the surgical site by being inserted into one of the pathways secured by the enlarging tubes;
   a root retractor comprising a first curved portion at a center of the root retractor, a second curved portion at an end of the root retractor configured to retract the muscle separated from the bone by the muscle detacher and to secure an additional working space and a grooved portion having a curvature facing opposite to a direction of curvature of the first curved portion; and
   an endoscope configured to be inserted into the body through a remaining one of the pathways secured by the enlarging tubes and to capture an image of the surgical site, wherein the endoscope includes a sheath mechanism provided with a guide tube configured to control the direction of a saline solution during the unilateral biportal endoscopy.

2. The surgical instrument set of claim 1, further comprising:
   a double ended retractor comprising a handle portion located between two opposite tip portions located at each end configured to be inserted into a space created by the muscle detacher and to detach a nerve root from a bone or ligamentum flavum, the double ended retractor being selectively used during the unilateral biportal endoscopic surgery.

3. The surgical instrument set of claim 1, further comprising:
   a bone chip cannula provided with a collecting portion configured to collect and concentrate bone chips supplied from outside, and a guide tube portion connected to the collecting portion and extending in a lengthwise direction thereof, the guide tube portion configured to guide the bone chips to a disc in a state of reaching the surgical site through one of the pathways; and
   a bone chip impactor comprising a tip portion at a front end and a handle portion at an end opposite of the tip portion configured to impact on the bone chips guided to a disc space such that the bone chips are seated in the disc.

4. The surgical instrument set of claim 1, wherein the guide tube comprises a plurality of projections and a plurality of depressed portions at a front end which are configured to control the direction of a saline solution during the unilateral biportal endoscopy.

\* \* \* \* \*